(12) United States Patent
Steinberg (10) Patent No.: US 11,571,256 B2
(45) Date of Patent: Feb. 7, 2023

(54) IMAGE BASED PATHOLOGY PREDICTION USING ARTIFICIAL INTELLIGENCE

(71) Applicant: MAZOR ROBOTICS LTD., Caesarea (IL)

(72) Inventor: Shlomit Steinberg, Tel Aviv (IL)

(73) Assignee: MAZOR ROBOTICS LTD., Caesarea (IL)

( * ) Notice: Subject to any disclaimer, the term of this patent is extended or adjusted under 35 U.S.C. 154(b) by 738 days.

(21) Appl. No.: 16/509,630

(22) Filed: Jul. 12, 2019

(65) Prior Publication Data

US 2020/0038109 A1 Feb. 6, 2020

Related U.S. Application Data

(63) Continuation-in-part of application No. PCT/IL2018/050051, filed on Jan. 11, 2018.

(Continued)

(51) Int. Cl.
*G06G 7/58* (2006.01)
*G06K 9/00* (2022.01)
(Continued)

(52) U.S. Cl.
CPC .............. *A61B 34/10* (2016.02); *G06F 17/18* (2013.01); *G06T 7/0012* (2013.01); *G16H 50/30* (2018.01);
(Continued)

(58) Field of Classification Search
CPC .............. G06K 9/00; A61B 34/10; G06G 7/58
(Continued)

(56) References Cited

U.S. PATENT DOCUMENTS 6,980,922 B2 9/2005 Henderson et al.
8,073,521 B2 12/2011 Liew et al.
(Continued)

FOREIGN PATENT DOCUMENTS

CN 105611884 5/2016
CN 106137305 11/2016
(Continued)

OTHER PUBLICATIONS

Extended Search Report for European Patent Application No. 18738471.4, dated Oct. 5, 2020, 14 pages.
(Continued)

*Primary Examiner* — Seyed H Azarian
(74) *Attorney, Agent, or Firm* — Sheridan Ross P.C.

(57) ABSTRACT

A method for determining an acceptable spinal surgical plan for a subject using pathology prediction, comprising generating a potential spinal surgical plan, obtaining clinically relevant data of the subject, obtaining pre-operative three-dimensional images of a spinal region of the subject, determining relationships between pairs of vertebrae in the images, predicting relationships between pairs of vertebrae that are expected from the surgical plan, accessing a multiple patient database, obtaining sets of data from the database for patients with similar characteristics to the subject, determining risks of pathology types for the subject, using artificial intelligence to combine the determined risks to calculate an overall risk for pathology types for the subject, and if the overall risks are unacceptable, selecting an alternative spinal surgical plan, and if the said overall risks are acceptable, determining that said surgical plan is acceptable.

19 Claims, 6 Drawing Sheets

Related U.S. Application Data (60) Provisional application No. 62/445,285, filed on Jan. 12, 2017.

(51) Int. Cl.
*A61B 34/10* (2016.01)
*G16H 50/30* (2018.01)
*G06F 17/18* (2006.01)
*G06T 7/00* (2017.01)

(52) U.S. Cl.
CPC ............... *A61B 2034/105* (2016.02); *G06T 2207/30012* (2013.01)

(58) Field of Classification Search
USPC ....... 382/100, 103, 106, 128–132, 153, 156, 382/162, 168, 173, 181, 189, 199, 219, 382/224, 254, 276, 285, 291, 305, 312; 705/2; 703/11, 22
See application file for complete search history.

(56) References Cited

U.S. PATENT DOCUMENTS

| | | | |
|---|---|---|---|
| 8,126,234 | B1 | 2/2012 | Edwards et al. |
| 8,126,736 | B2* | 2/2012 | Anderson ............... A61B 34/10 705/2 |
| 8,818,484 | B2 | 8/2014 | Liew et al. |
| 9,700,292 | B2 | 7/2017 | Nawana et al. |
| 9,754,369 | B2* | 9/2017 | Weiss .................... G06T 7/0012 |
| 2009/0143788 | A1 | 6/2009 | Fang et al. |
| 2010/0191071 | A1* | 7/2010 | Anderson ............... G16H 50/50 703/11 |
| 2013/0173240 | A1 | 7/2013 | Koell et al. |
| 2014/0081659 | A1 | 3/2014 | Nawana et al. |
| 2016/0030131 | A1 | 2/2016 | Wang et al. |
| 2017/0337682 | A1* | 11/2017 | Liao ..................... A61B 5/7267 |
| 2019/0216452 | A1* | 7/2019 | Nawana ................ A61B 5/7282 |
| 2021/0280299 | A1* | 9/2021 | Weiss ..................... B60R 25/00 |

FOREIGN PATENT DOCUMENTS

| | | |
|---|---|---|
| JP | 2016-093497 | 5/2016 |
| WO | 2005088520 A1 | 9/2005 |
| WO | 2015176011 A1 | 11/2015 |

OTHER PUBLICATIONS

Corresponding PCT application PCT/IL2018/050051—Search report and written opinion dated Apr. 12, 2018.

Jin R, et al. "A machine learning based prognostic prediction of cervical myelopathy using diffusion tensor imaging" University of Hong Kong Jul. 28, 2016.

Ratliff JK, et al. "Prediction occurrence of spine surgery complications using big data modeling of an administrative claims database." May 18, 2016.

Mannion AF. "Predictors of surgical outcome and their assessment." Dec. 1, 2005.

Tighe PJ, Harle CA. "Teaching a machine to feel postoperative pain combining high-dimensional clinical data with machine learning algorithms to forecast acute postoperative pain." Jul. 1, 2015.

Maruo K et al. Predictive factors for proximal junctional kyphosis in long fusions to the sacrum in adult spinal deformity. Spine, vol. 18, No. 23 pp. E1469-E1476.

Schlenk RP et al. "Biomechanics of spinal deformity." Neurosurg Focus 14(1), Article 2, 2003.

Nyugen NLM et al. "Proximal junctional kyphosis and failure—diagnosis, prevention and treatment." Curr Rev Musculoskel Med 9, pp. 299-308, 2016.

Official Action with English Translation for China Patent Application No. 201880012118.2, dated Mar. 11, 2022, 12 pages.

Official Action with English Translation for China Patent Application No. 201880012118.2, dated Aug. 31, 2022, 19 pages.

* cited by examiner

IMAGE BASED PATHOLOGY PREDICTION USING ARTIFICIAL INTELLIGENCE

RELATED APPLICATIONS

This disclosure claims priority to PCT/IL2018/050051, titled "IMAGE BASED PATHOLOGY PREDICTION USING ARTIFICIAL INTELLIGENCE and filed on Jan. 11, 2018, which in turn claims priority to U.S. Provisional Patent Application No. 62/445,285, titled "IMAGE BASED PATHOLOGY PREDICTION USING ARTIFICIAL INTELLIGENCE and filed on Jan. 12, 2017. The contents of both applications are incorporated herein by reference in their entireties and for all purposes.

RELEVANT FIELD

Embodiments of the present disclosure relate to the field of image based pathology prediction for planning spinal surgery, using predictive modeling such as machine learning, deep learning or any statistical method that can be used to predict outcomes.

BACKGROUND

Long term surgical outcomes of spinal surgery are difficult to predict due to the many factors involved and their sophisticated relationships. Avoiding the development of post-operative junctional complications and pathologies is an important challenge in spinal deformity surgeries. Among the pathologies that may develop post operatively over time, some common pathologies are:
  Adjacent level degeneration—Advanced disc degeneration or segmental instability above a surgical fusion
  Adjacent segment disease—Pathology adjacent to a surgical fusion that creates symptoms of pain and/or nerve compression that leads to revision surgery
  Proximal junctional kyphosis—Radiographic measure of greater than 5 degrees of progression of segmental kyphosis above a fusion
  Proximal Junctional Failure—10° post-operative increase in kyphosis between upper instrumented vertebra (UIV) and UIV+2
  Kyphotic Decompensation Syndrome—Progressive sagittal deformity requiring revision surgery for realignment of the spine These pathologies may develop many months, years or even decades after a surgery, often requiring revision surgery. Furthermore, after a period of time following the surgery, post-operative instrumentation failures may occur, such as screw pull-out and implant breakage.

Today it is understood that the development of pathologies and instrumentation failures, such as those listed above, is strongly related to preoperative and post-operative spinal parameters as may be determined from three-dimensional images, as well as to the degree of anatomical adjustment during the surgery, and that a planned spinal surgical technique should take these factors into consideration, in addition to other clinically relevant patient specific risk factors.

Some references describe image based prediction methods that use comparison of image derived and non-image derived subject data to databases. For example, U.S. Pat. No. 8,818,484 to S-W Liew et al, for "Methods of predicting musculoskeletal disease" discloses methods of predicting bone or joint disease in a subject. U.S. Pat. No. 8,073,521 to S-W Liew et al, for Method for bone structure prognosis and simulated bone remodeling" discloses, among other methods, methods for estimating fracture risk in a subject. U.S. Pat. No. 6,980,922 for "Computer simulation model for determining damage to the human central nervous system" to S. C. Henderson describes a computerized model that simulates the human spinal cord and makes it possible to draw inferences about the probability of future injury. However, these references do not attempt to make correlations between a proposed surgical plan and its associated risk of pathology or instrument failure, nor does it provide a method for determining an acceptable surgical plan using image based pathology or instrument failure prediction.

Other references explore risk factors for development of pathologies, but such references usually focus on only one specific category of risk factors. For example, the article "Predictive factors for proximal junctional kyphosis in long fusions to the sacrum in adult spinal deformity" by Maruo K. et al published in SPINE, Vol. 38, No. 23, pp E1469-E1476, explores the relationships between pre-operative and post-operative spinal parameters and the risk of pathology onset. This reference states "Fracture at the UIV was the most common mechanism for PJK. Change in LL more than 30° and pre-existing TK more than 30° were identified as independent risk factors. Optimal postoperative alignment of the spine protects against the development of PJK. A surgical strategy to minimize PJK may include preoperative planning for reconstructions with a goal of optimal postoperative alignment." Another reference, "Minimally Invasive Spinal Deformity Surgery: An Evolution of Modern Techniques", edited by Michael Y. Wang et al, published by Springer-Verlag Wien 2014, focuses on past medical history and previous surgeries of a subject as important risk factors to consider when planning a spinal surgery.

"Biomechanics of spinal deformity" by Shlenk et al, Neurosurg. Focus, Vol. 14, January, 2003 states "Pathological spinal deformation, either in an acute or chronic form, is usually a result of at least one unstable motion segment." This reference describes "six fundamental segmental movements of the spine along or around the IAR [Instantaneous Axis of Rotation] can occur: 1) rotation or translation around the long axis; 2) rotation or translation around the coronal axis; 3) rotation or translation around the sagittal axis of the spine; 4) translation along the long axis of the spine; 5) translation along the coronal axis; and 6) translation along the sagittal axis of the spine (FIG. 2). Each movement may result in deformation in one of two directions involving one or many spinal segments as a result of acute chronically applied loads." However, this reference simply categorizes the deformity types, and does not provide a method for determining an acceptable surgical plan using image based pathology or instrument failure prediction.

U.S. Pat. No. 9,700,292 for "Systems and methods for surgical and interventional planning, support, post-operative follow-up, and functional recovery tracking" to N. Nawana et al, describes a system that "can provide recommendations regarding diagnosis, non-surgical treatment, surgical treatment, and recovery from the surgical treatment based on data gathered from the patient and the medical professional(s)." This reference describes methods for surgical planning including use of databases, but does not appear to provide specific methods for defining vertebral pair relationships, or to use such defined relationships in a spinal surgical planning method that predicts the likelihood of one or more pathology types, and optionally the likelihood of one or more instrument failure types, associated with a specific surgical plan for a selected subject.

The article entitled "Proximal junctional kyphosis and failure-diagnosis, prevention, and treatment" by Ngoc-Lam M. Nguyen et al, Published online 9 Jun. 2016 by Springer Science and Business Media, New York 2016, summarizes the problem in stating "Agreement on the definition, classification, and pathophysiology of PJK and PJF remains incomplete, and an understanding of the risk factors, means of prevention, and treatment of this problem remains to be elucidated." Thus, a comprehensive approach for spinal surgical planning is needed that takes into account the many types of pathology risk factors involved, and especially that accurately predicts long term outcomes of a spinal surgical plan.

There therefore exists a need for a method of predicting future pathologies based on image analysis, using predictive modeling such as machine learning, deep learning or any other statistical method that can be used to predict outcomes, operating on large databases of previously obtained data for similar procedures, which overcomes at least some of the disadvantages of existing methods.

The disclosures of each of the publications mentioned in this section and in other sections of the specification, are hereby incorporated by reference, each in its entirety.

SUMMARY

Embodiments shown in the present disclosure describe new exemplary methods for determining if a spinal surgical plan is acceptable for a subject by predicting likelihood of a poor surgical outcome which may be at least one of (i) an associated subject-specific likelihood of development of one or more pathology types or (ii) an associated subject-specific likelihood of one or more instrument failure types, using analysis of data, mined from a large database, that is similar to that of the subject. Some of the disclosed methods predict these risks using analysis of the relationships of pairs of vertebrae, according to predefined parameters, in three-dimensional pre-operative images of the subject, analysis of clinically relevant quantitative data of the subject, analysis of a surgical plan, and analysis of post-operative vertebral pair relationships as derived from a predictive simulation. In surgical plans that require instrumentation, additional analysis of the expected relationships of instrumentation to vertebral pairs may be performed. Artificial intelligence or machine learning is advantageously used in these analyses and predictions to identify the most highly correlated or useful vertebral pairs and vertebral relationships for prediction, and to allow for a multiple tiered risk calculation approach, with the processor-based system being capable of combining multiple parallel probabilities based on different risk factors in an accurate manner, and being capable of improving its accuracy over time.

There is thus provided in accordance with an exemplary implementation of the methods described in this disclosure, a method for determining an acceptable surgical plan for a subject, using long term pathology prediction, the method comprising:
(i) generating a spinal surgical plan that is to be performed on an operative region,
(ii) obtaining clinically relevant quantitative data of the subject,
(iii) obtaining pre-operative three-dimensional images of a spinal region of interest of the subject,
(iv) determining relationships between selected pairs of vertebrae in the pre-operative three-dimensional images, with at least some of the relationships being determined for vertebrae outside of the operative region,
(v) predicting relationships between at least some of the selected pairs of vertebrae that are expected from the spinal surgical plan,
(vi) accessing a database including data for a plurality of patients, with data for each patient comprising data on any pathology types developed, and additional data on at least one of the associated (a) pre-operative images, (b) post-operative images, (c) clinically relevant quantitative data, or (d) surgical plan,
(vii) obtaining from the database, one or more sets of data for patients with similar characteristics as those of at least one of options (a) (b) (c) or (d) of step (vi),
(viii) determining risks of one or more pathology types for the subject based on correlations of the patients in at least some of the sets, to developed pathology types, and
(ix) using artificial intelligence to combine the previously determined risks, to calculate an overall risk for one or more pathology types for the subject.

According to a further implementation of the above described method, if the one or more overall risks are unacceptable, an alternative spinal surgical plan may be selecting and the procedure returned to step (v).

Additionally and optionally, the overall risk can be output by the system, so that it can be used for assessing the success of the iteration, and hence used to determine the acceptability of the surgical plan.

In the above method, the clinically relevant quantitative data may be derived from qualitative data. Additionally, the spinal region of interest of the subject may be more extensive than the operative region of the spinal surgical plan.

According to further implementations of this method, the data for each patient of step (vi) may further comprise data on any instrument failure types developed, and the method may further comprise calculating an overall risk for one or more instrument failure types for a spinal surgical plan for the subject. Such instrument failure types may comprise at least one of screw pull-out, excessive rod bending, or fractures or breakage of any of implants, screws, interbodies and rods.

Furthermore, in accordance with either of the above described methods, the relationships between selected pairs of vertebrae may comprise one or more of (i) angle between endplates, (ii) distance between vertebrae, (iii) shape or volume of intervertebral space, and (iv) degree of rotation or translation of a vertebra relative to the long axis of the spine, coronal axis of the spine, or sagittal axis of the spine, relative to this measurement for an adjacent vertebra.

In any of the above described methods, one or more of the relationships between selected pairs of vertebrae may involve characteristics of a disc between a vertebral pair.

Additionally, the pre-operative three-dimensional images may be any of CT images, MRI images, X-ray images, and dynamic motion capture images.

Additionally, alternative implementations of any of the above-described methods may further involve a situation in which the clinically relevant quantitative data comprises at least one of (i) past medical history, (ii) age, (iii) BMI, (iv) gender, (v) comorbidity, (vi) ethnicity, or (vii) current clinical status.

Furthermore, the database may additionally comprise an approximate date of onset of pathology for at least some of the plurality of patients, and step (viii) mentioned above may further comprise determining risks of the subject developing one or more pathology types at defined time points in the future. In such cases, the method may further comprise calculating conditional probabilities of the subject developing one or more pathology types at defined time points in the future, based on different combinations of risk factors. These defined time points in the future may comprise any of half a year after the surgery, a year after the surgery, 2 years after the surgery, 5 years after the surgery, 10 years after the surgery, and 15 years after the surgery.

Additional implementations may involve any of the above methods, in which the above described step (viii) is performed using artificial intelligence, predictive modeling or any statistical methods such as any of machine learning, deep learning, neural networks, and regressions.

According to any of the above described methods, the step of determining if the one or more overall risks are acceptable is performed by a processor-based system according to predefined rules. Additionally, the correlations of the patients in each of the previously mentioned sets, to developed pathology types may be performed using at least one of Pearson correlation coefficient, Pearson's product-moment coefficient, linear regression analysis, or Spearman rank correlation.

Furthermore, in the above mentioned step (vii), the one or more sets of data for patients with similar characteristics may comprise a set of data for patients with similar characteristics as those of the above mentioned pre-operative images and surgical plan, and another set of data for patients with similar characteristics as those of the above mentioned post-operative images. Additionally, in the above mentioned step (vii), the one or more sets of data for patients with similar characteristics may comprise multiple sets, with at least some of the multiple sets each having similar characteristics to any one of the above mentioned pre-operative images, post-operative images, clinically relevant quantitative data, and surgical plan.

In yet further implementations of the above described methods, in step (iii), the pre-operative three-dimensional images of a spinal region of interest of the subject may include a region of planned instrumentation.

Additionally, the above described step (v) may further comprise predicting relationships that are expected between at least some of the selected pairs of vertebrae and a planned instrumentation.

Finally, in any of these methods, the step of determining the probability for the one or more overall risks may be performed using machine learning.

To be clear, and as one of skill in the art will appreciate upon reading the instant disclosure, the term system may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components, such as optical, magnetic, or solid state drives, that provide the described functionality; or a combination of some or all of the above, such as in a system-on-chip. The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this disclosure may be partially or fully implemented by one or more computer programs executed by one or more processors. The computer programs include processor-executable instructions that are stored on at least one non-transitory tangible computer readable medium. The computer programs may also include and/or rely on stored data.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

BRIEF DESCRIPTION OF DRAWINGS

Embodiments shown in the present disclosure will be understood and appreciated more fully from the following detailed description, taken in conjunction with the drawings in which.

DETAILED DESCRIPTION

Figure 1:
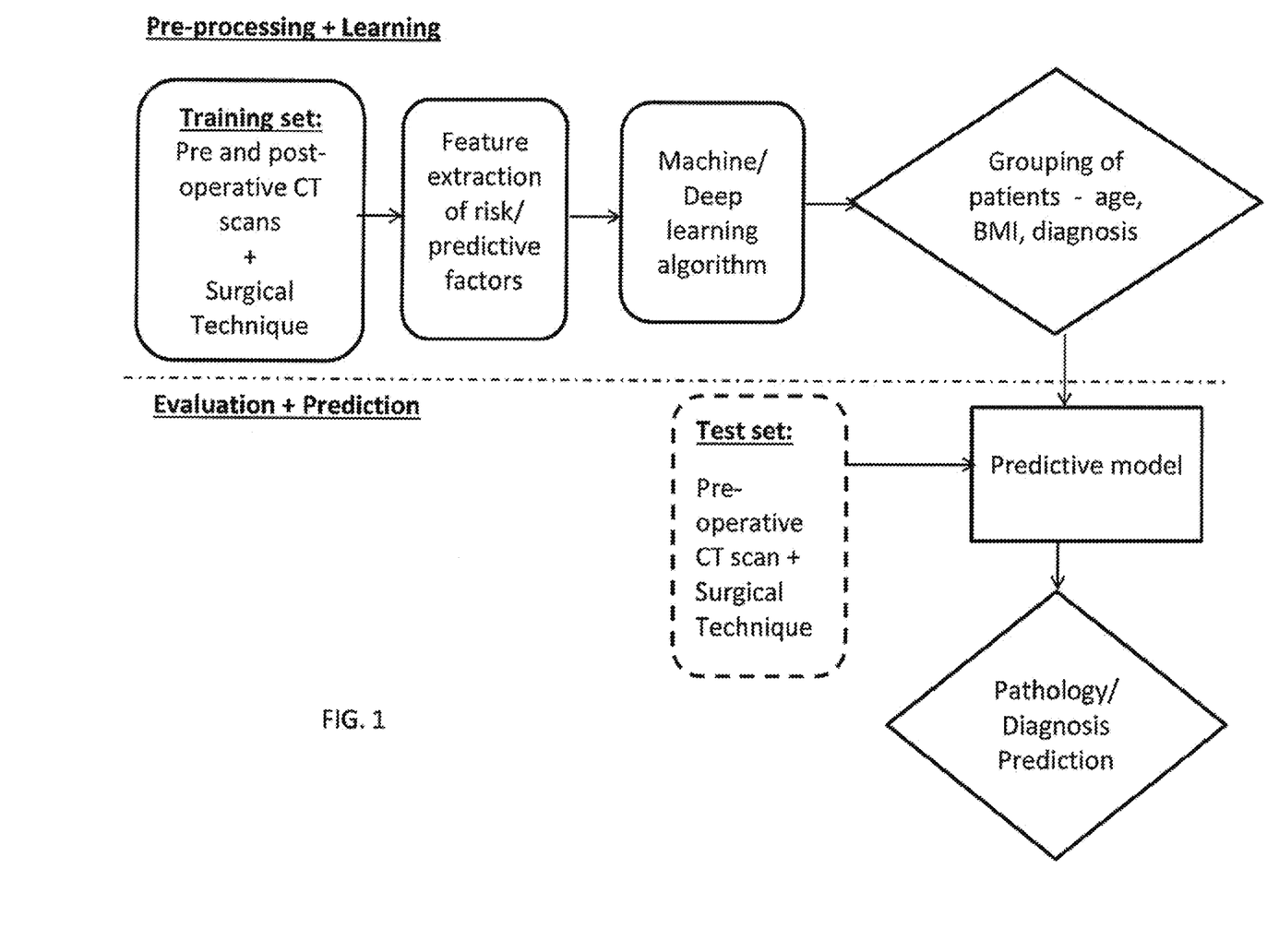
FIG. 1 shows a conceptual overview of exemplary methods of the present disclosure for machine learning and prediction for a subject based thereon.

Reference is now made to FIG. 1, showing a conceptual overview of exemplary methods of the present disclosure for machine learning, and prediction for a subject based thereon. The method commences with assembly of a training set of data for a processor-based system for pre-processing and learning. The training set includes data on a plurality of patients, and data for each patient may include, inter alia, pre-operative three-dimensional images, post-operative three-dimensional images, surgical technique used, clinically relevant quantitative data, and any pathologies or instrument failures developed, and may advantageously include those developed after a long time period following the surgery. The system may then find correlations in the training set between certain risk factors and defined negative clinical outcomes, and uses these correlations to extract a plurality of risk factors that are determined to be relevant for prediction. A deep learning algorithm is then used to determine which of these extracted risk factors, and combinations of risk factors, are likely to result in a developed pathology, instrument failure, or other negative clinical outcome. The learning algorithm is then used to group the patients in the training set according to their individual risk factors, such as their age, BMI, and diagnosis.

A predictive model is now complete, and a test set for a new selected subject may be input into the system, which may include, inter alia, the subject's pre-operative three-dimensional images, such as CT scans, and the planned surgical technique. The predictive model may then be used to predict a likelihood of the subject developing one or more pathologies or instrument failures, given the planned surgical technique. The predictive model may additionally be used for diagnosis of the subject. The method may include the additional step of selecting a new surgical technique for prediction analysis, should the risks be determined to be unacceptable. Furthermore, the data from the test set may be incorporated into the database, and machine learning algorithms may be applied to the newly expanded database for more accurate prediction of pathology or instrument failure development in future subjects. The use of large data sets and deep machine learning in the disclosed methods overcome the difficulties of existing methods that focus on limited, specific risk factors, by instead performing a comprehensive analysis on large numbers and types of risk factors.

Figure 2:
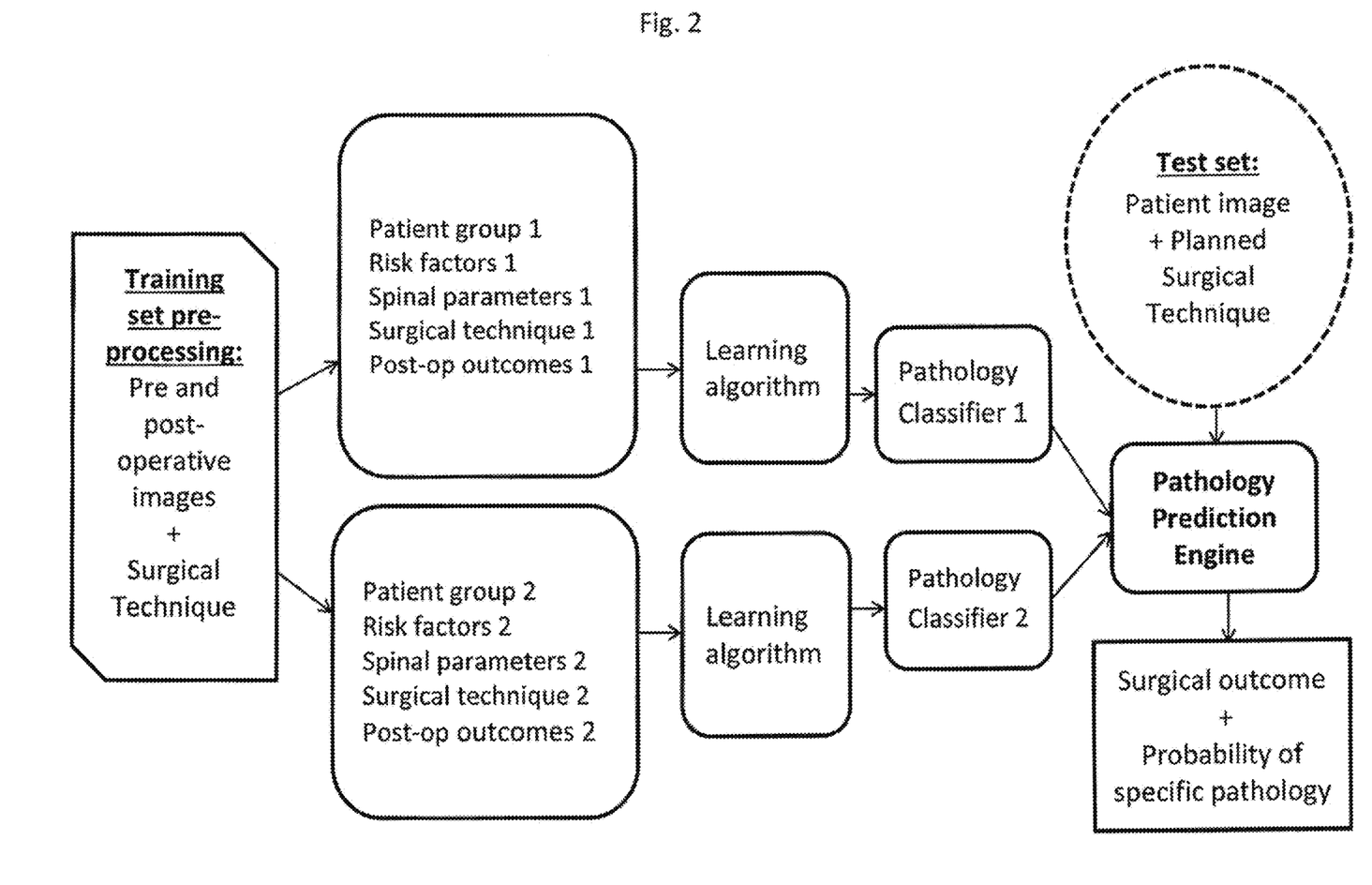
FIG. 2 shows a conceptual overview of exemplary methods of the present disclosure for machine learning having multiple learning algorithms and multiple pathology classifiers, and prediction for a subject based thereon.

Reference is now made to FIG. 2, which shows a conceptual overview of exemplary methods of the present disclosure for machine learning having multiple learning algorithms and multiple pathology classifiers, and prediction for a subject based thereon. This exemplary method shows two different learning algorithms and two pathology classifiers, but alternative methods of the present disclosure may advantageously involve sophisticated systems that are capable of producing many more. The method commences with input of a training set of data for pre-processing, comprising data related to a plurality of patients. Such data may comprise, inter alia, pre-operative images, post-operative images, surgical technique, clinically relevant quantitative data, and development of pathology or instrument failure. The patients in the training set are then grouped according to different post-operative outcomes, with each group comprising data on, inter alia, the risk factors, spinal parameters, and surgical technique used for the patients in the group. The system then employs learning algorithms to classify data in the groups according to pathology classifiers, in this example, classifiers 1 and 2. This step may be performed by finding patterns or correlations within the groups between risk factors and developed pathologies or instrument failures. The combination of the pathology classifiers in some embodiments is the pathology prediction engine, or the predictive model.

Once the prediction engine has been sufficiently developed, a test set for a subject may be input into the system comprising, inter alia, the subject's pre-operative three-dimensional images and a planned surgical technique for prediction analysis. The pathology prediction engine then provides the expected surgical outcome for the subject, and the probability of the subject's development of one or more specific pathology or instrument failure types, given the planned surgical technique. The method may include the additional step of selecting a new surgical technique for prediction analysis, should the risks be determined to be unacceptable. Furthermore, the data from the test set may be incorporated into the database, and machine learning algorithms may be applied to the newly expanded database for more accurate prediction of pathology or instrument failure development in future subjects.

Figure 3A:
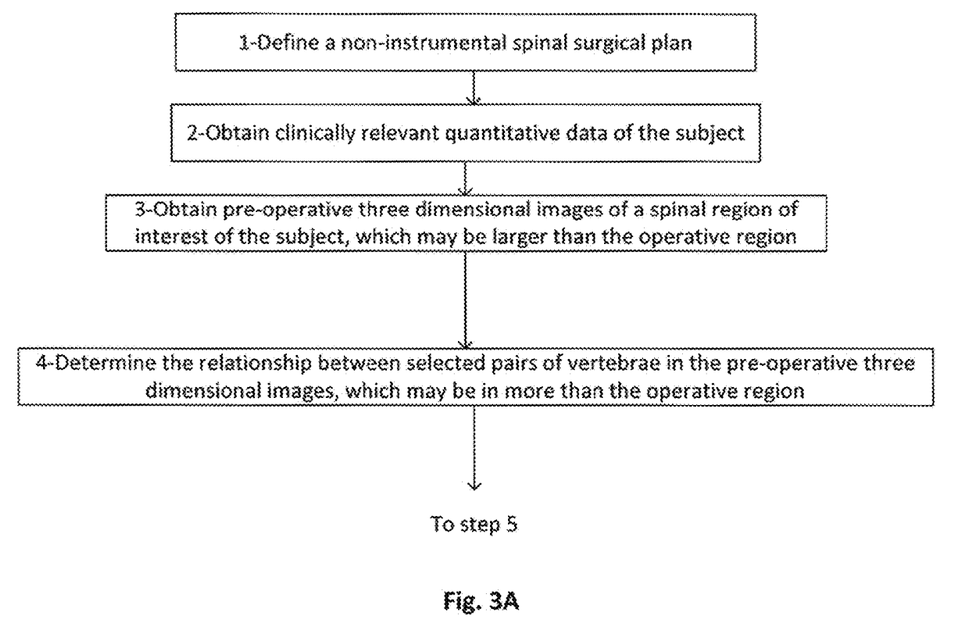
FIGS. 3A and 3B show details of an exemplary method for determining if a non-instrumental spinal surgical plan is acceptable for a subject.
Figure 3B:
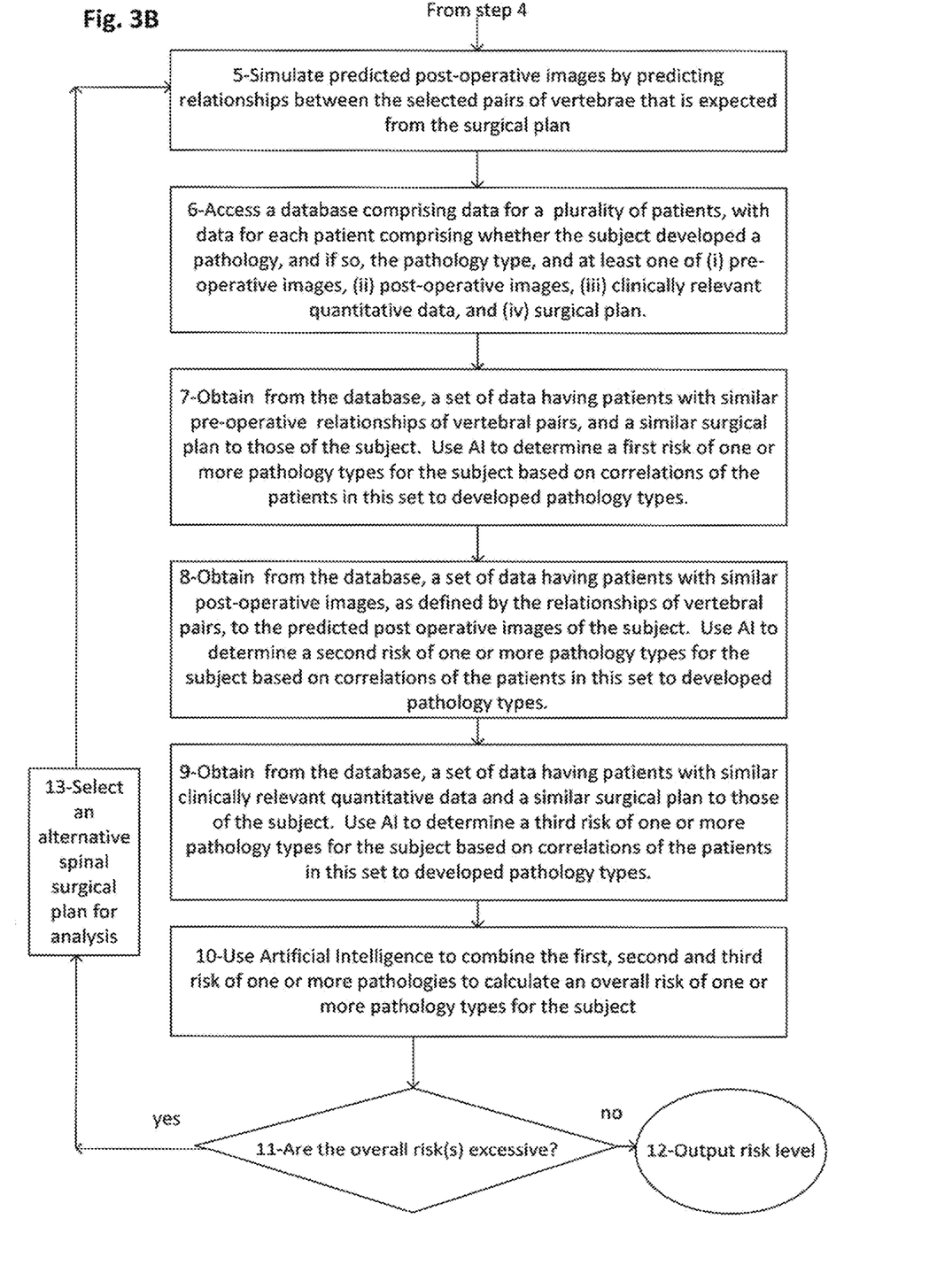

Reference is now made to FIGS. 3A and 3B, which show an exemplary method for determining if a non-instrumental spinal surgical plan acceptable for a subject, by predicting the likelihood that the subject will develop one or more pathology types after the surgical plan has been performed on the subject.

In step 1, a non-instrumental spinal surgical plan is selected for pathology prediction analysis. Exemplary pathologies for prediction include neuromuscular pathologies and degenerative pathologies, which may be comprised within a database. The selected surgical plan may include the location of surgery, and vertebrae involved in the surgery.

In step 2, clinically relevant quantitative data of the subject is obtained, such as, inter alia, any pre-operative pathologies, age, BMI, gender, bone density, vitamins rate, comorbidity, ethnicity demographics, vitals, medical history, history of illnesses, complaints, anamneses, test results, diagnosis, medications, and past medical history which may include previous surgeries. The term quantitative data is understood to include quantification of subjective or qualitative data provided by the subject.

In step 3, pre-operative three dimensional images of a spinal region of interest of the subject are obtained, with such a region of interest possibly being larger than the operative region. The three-dimensional images may be CT images, MRI images, or X-ray images, and the region of interest may include the entire spine, or may include as large a portion of the spine as possible. Alternatively or additionally, dynamic motion capture images of the subject may be obtained, which allows for any pathology risk factors related to the subject's motion to be derived.

In step 4, relationships are determined between selected pairs of vertebrae in the pre-operative three-dimensional images, where at least some of these relationships may be determined for vertebrae outside of the operative region. By incorporating vertebrae outside of the operative region, the method takes into consideration pathologies that may arise from more extensive spinal misalignment. The relationships between vertebrae are based on predefined parameters, and may include one or more of measurements between vertebral endplates, shape or volume of vertebra, distance between vertebrae, shape or volume of intervertebral space or characteristics of a disc between a vertebral pair, and degree of rotation or translation of a vertebra around the long axis of the spine, coronal axis of the spine, or sagittal axis of the spine, relative to the this measurement for an adjacent vertebrae. In order to calculate these parameters, coronal and sagittal plane segmentation may be performed on the three-dimensional images, providing an approximate relative position and orientation of each vertebrae, and the coronal, sagittal and long axes of the spine may likewise be identified in the images. Additional image derived data may be obtained during this step, such as vertebral range of motion parameters, dynamic movement parameters, spinal alignment, bone quality or density, and anatomical alignment parameters.

In step 5, a simulation of predicted post-operative three-dimensional images is generated by predicting relationships between the selected pairs of vertebrae that are expected from the selected surgical plan. The relationships between vertebrae are based on predefined parameters, as described hereinabove.

In step 6, a database (e.g., a tangible, non-transitory, computer-readable storage medium) is accessed. The database comprises data for a plurality of patients, with data for each patient comprising whether the subject developed a pathology, and if so, the pathology type, and at least one of (i) pre-operative images, (ii) post-operative images, (iii) clinically relevant quantitative data, or (iv) surgical plan. The data for each patient may further comprise the date or approximate time at which the patient developed a pathology. The data for each patient may further comprise images taken at different times following the surgery, for example, images taken 2, 5, 10, or 15 years after the surgery.

In step 7, it is obtained from the database, a set of data having patients with similar pre-operative relationships of vertebral pairs, and a similar surgical plan, to those of the subject. Artificial intelligence may be employed to determine a first risk of one or more pathology types for the subject based on correlations of the patients in this set to developed pathology types. Optionally, a risk may be provided for a time of onset for each pathology.

In step 8, it is obtained from the database, a set of data having patients with similar post-operative relationships of vertebral pairs to the vertebral relationships in the predicted post-operative images of the subject. Artificial intelligence may be employed to determine a second risk of one or more pathology types for the subject based on correlations of the patients in this set to developed pathology types. Optionally, a risk may be provided for a time of onset for each pathology, generally with the date of the surgery being the defining reference point.

In step 9, it is obtained from the database, a set of data having patients with similar clinically relevant quantitative data and a similar surgical plan to those of the subject. Artificial intelligence may be employed to determine a third risk of one or more pathology types for the subject based on correlations of the patients in this set to developed pathology types. Optionally, a risk may be provided for a time of onset for each pathology, generally with the date of the surgery being the defining reference point.

It is understood that steps 7 to 9 represent exemplary tiers of risk factor combinations, and that additional or alternative tiers may be used. The use of tiers provides a novel approach to the prediction analysis of embodiments of the present disclosure by separating risk factors so as to accurately identify correlations associated with each risk factor or combinations of risk factor, and to identify relationships between the correlations. This is an advantageous approach that analyzes all or most of the risk factors together in a single analysis, thereby potentially increasing the risk of confounding variables and concealing root causes and relationships that are relevant for prediction. Of the possible combinations of tiers, a particularly advantageous combination of tiers uses analysis in parallel of (i) a set of data having patients with similar pre-operative relationships of vertebral pairs, and a similar surgical plan to those of the subject, and (ii) a set of data having patients with similar post-operative images to the predicted post-operative images of the subject. This may provide two similar probabilities of pathology for the subject, but each set may comprise data on different sets of patients, and the distinctions between the outcomes of the parallel analyses may be critical for prediction. For example, if the set of the patients with similar pre-operative images and a similar surgical plan had a 20% rate of development of Proximal Junctional Kyphosis, and the set of patients with similar post-operative images had a 30% rate of development of Proximal Junctional Kyphosis, then this discrepancy may be further analyzed or interpreted in a variety of ways using Artificial Intelligence. As one limited example, there may be a nuanced difference between the surgical plan used in set (i) and the plan used in simulation of the expected post-operative images of the subject for comparison to set (ii), and this nuanced difference may be a crucial link in selecting a surgical plan for a subject that is likely to avoid development of PJK.

As one limited example, a pre-operative image of the selected subject may be virtually altered to simulate the expected change in anatomy over time (e.g. in 20 years), including the natural effects of aging, either with or without undergoing a specific surgery. This altered image may then be input into a system having a database and compared to data of similar patients, and data regarding whether these similar patients have a specific pathology, for determining the probability of the selected subject developing this pathology. This method may be advantageous for long term predictions over many years or decades, since natural aging is considered to be a risk factor for many spinal pathologies.

The above described correlations of image derived data and quantitative data may be performed using any of various suitable correlation coefficients such as Pearson correlation coefficient, Pearson's product-moment coefficient, linear regression analysis, Spearman Rank Correlation, etc. Analysis of variance permits testing of differences among sample groups to determine whether a selected variable has a discernable effect on the parameters being measured.

Data may be aggregated, sorted, selected, sifted, clustered and segregated by means of the attributes associated with the data points to allow the system to find correlations. Distribution curves can be established and the mean, median and mode calculated. Data spread characteristics, e.g., variability, quartiles and standard deviations can be calculated. Data mining software can use tools such as cluster analysis, factor analysis, decision trees, neural networks, rule induction, data driven modeling, and data visualization. All patient-specific correlations may be organized to construct a dynamically improving predictive model for each surgery type/pathology combination. This may involve eliminating weak correlations, or considering statistical significance, for example. Tests for statistical significance include the Chi-Square test, the Chi-Square Goodness of Fit, the 2×2 contingency table, the Sign Test, and the Phi Correlation Coefficient.

For long term predictions, conditional probabilities may be applied. For example, the probability that subject X will develop pathology P 20 years after surgery is 50% conditional on that he does not have an occupation involving lifting heavy objects during those 20 years, but is 60% conditional on that he has an occupation involving lifting heavy objects for at least 5 out of the 20 years. In some cases, where there is little variation within a range of data, it may be appropriate to assign a range of data to a "cloud". For example, patients 35-40 years old with a pre-operative deformity X have an average probability of 8% of developing pathology P.

In step 10, artificial intelligence or machine learning is used to combine the first, second, third, and any additional previously determined risks of pathology types, to calculate an overall risk of one or more pathologies for the subject. A risk may be provided for each pathology, such as in the form of a percentage. Optionally, a risk may be provided for a time of onset for each pathology, such as the probability that the subject will develop PJK ten years after the surgery.

A system may use the machine learning built predictive model using univariate, bivariate, or multivariate statistical analysis to output the probability of a selected patient developing one or more specific pathologies, such as adjacent level degeneration, adjacent segment disease, proximal or distal junctional kyphosis or failure, and kyphotic decompensation syndrome. The system may use the assigned predictive values to output an overall probability that he will develop a specific pathology at any point after the surgery during his lifetime, and/or the system may output the probability of developing a specific pathology at times X, Y, Z, etc., for example, 6 months, 1 year, 2 years, 5 years, 10 years, etc., after the surgery. If the probabilities are considered mutually exclusive, then this would be a simple calculation, e.g. P(A)|B, C and D. Alternatively, a more sophisticated method could calculate all relevant conditional probabilities, e.g. P(A)|B, C and D when P(B)|D is X percent.

In step 11, the system determines whether the one or more overall risks are excessive according to pre-defined rules of acceptability of overall risk level, for example, more than ten percent risk of any pathology.

If the risks are deemed excessive, this surgical plan is deemed unacceptable, and in step 12, an alternative spinal surgical plan is selected for pathology prediction analysis, and the system performs the selection routine again, and in step 13, the risk level result may optionally be output by the system.

Should the number of alternative spinal surgical plans exceed a predetermined level, the system may terminate the routine, since the sought-for surgical solutions selected may possibly be in an incorrect direction.

Figure 4A:
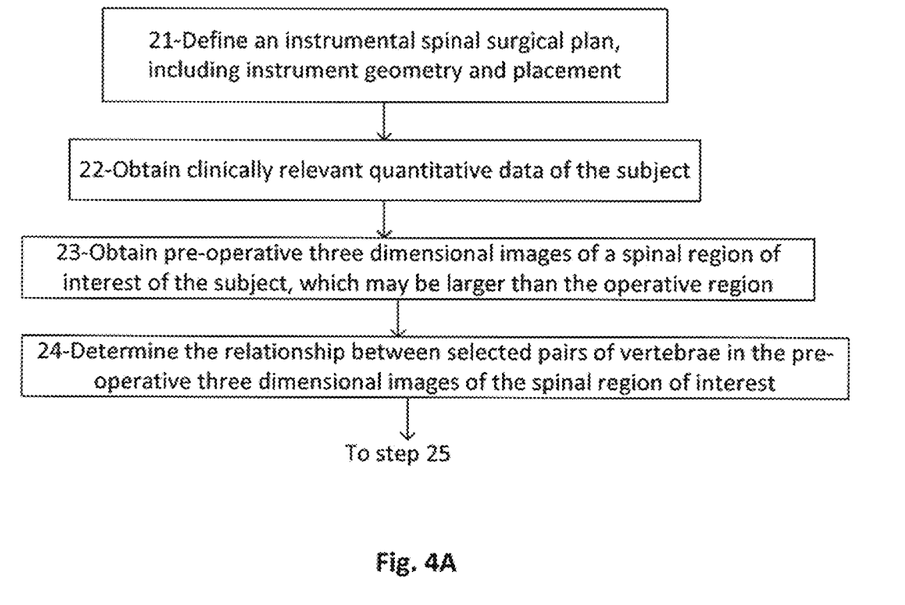
FIGS. 4A and 4B show details of an exemplary method for determining if an instrumental spinal surgical plan is acceptable for a subject.
Figure 4B:
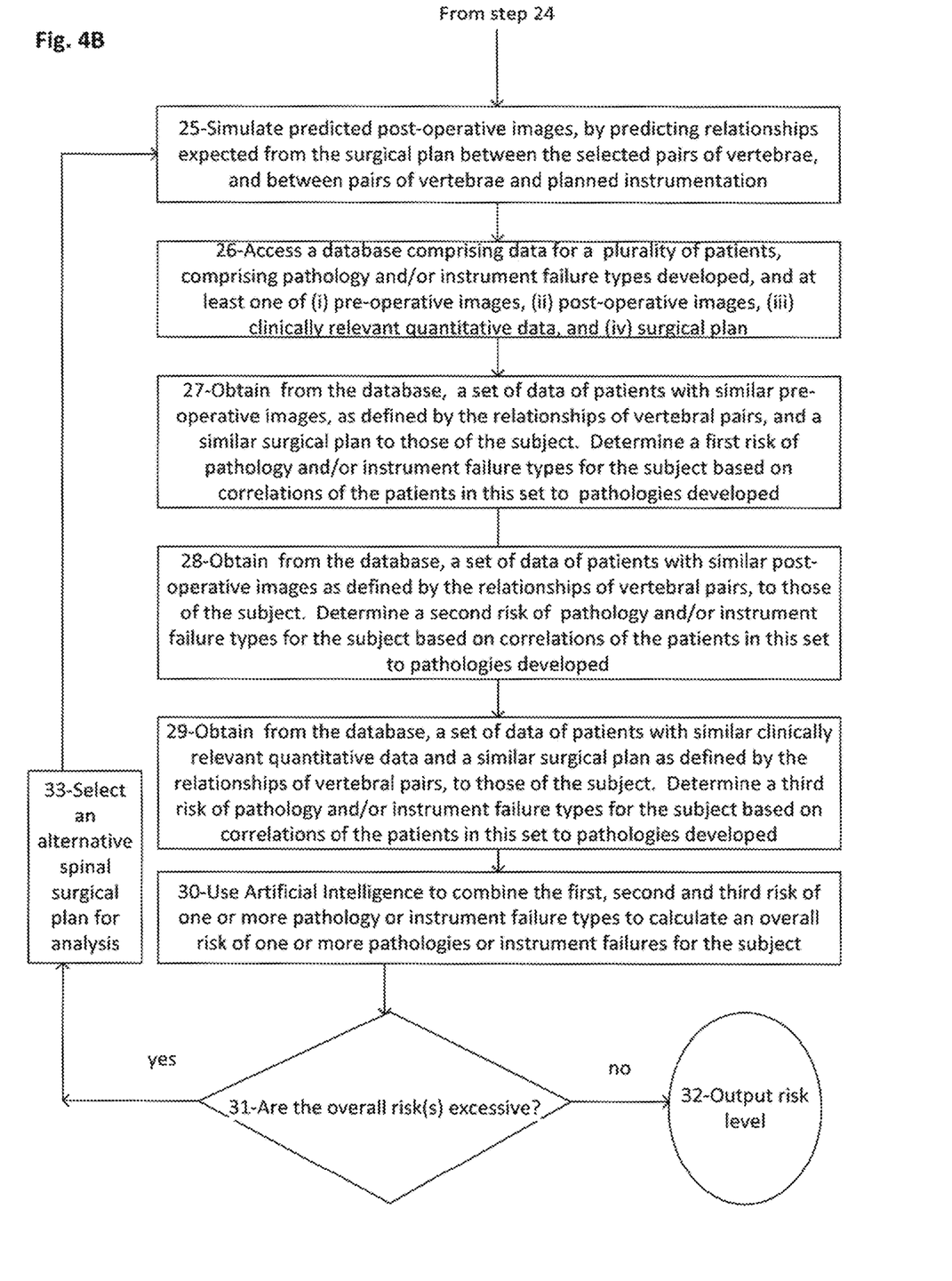

Reference is now made to FIGS. 4A and 4B, showing a method for determining if an instrumental spinal surgical plan acceptable for a subject, by predicting the likelihood that the subject will develop one or more pathology types or instrumental failures, such as screw pull-out, rod bending or breakage, implant loosening or the like, after the surgical plan has been performed on the subject.

In step 21, an instrumental spinal surgical plan is selected for a subject, including the instrument geometry and placement, for pathology and instrument failure prediction analysis. The surgical plan may include a choice of fusion level, rigidity of fixation, implants and interbody properties and placement, rod properties and osteotomy locations and angles. Exemplary pathologies for prediction include neuromuscular pathologies, degenerative pathologies, adjacent level degeneration, adjacent segment disease, distal junctional kyphosis, distal junctional failure, proximal junctional kyphosis, proximal junctional failure, and kyphotic decompensation syndrome, all of which may be comprised within a database. The selected surgical plan may include the level of instrumentation, instrumentation properties such as screw system, diameter, position in the vertebra, interbody size, angle, location in the intervertebral disc space and the like.

In step 22, clinically relevant quantitative data of the subject is obtained such as, inter alia, any pre-operative pathologies, age, BMI, gender, and ethnicity. The quantitative data may include quantification of subjective or qualitative data provided by the subject.

In step 23, pre-operative three-dimensional images are obtained of a spinal region of interest of the subject, in which the spinal region of interest may include more than the operative region.

In step 24, relationships are determined between selected pairs of vertebrae in the pre-operative three-dimensional images, with at least some of these relationships preferably being determined for vertebrae outside of the operative region. The relationships between vertebrae are based on predefined parameters, as described hereinabove.

In step 25, a simulation is performed that predicts the post-operative relationships between the selected pairs of vertebrae, and also between one or more instrument-associated pairs of vertebrae and the planned instrumentation, that is expected from the selected spinal surgical plan. This instrumentation-related parameters can include the angle of screws relative to the vertebra, the interbody location inside the disc space, the level of instrumentation, and the like.

In step 26, a database is accessed. The database comprises data for a plurality of patients, with data for each patient comprising whether the subject developed either or both of a pathology or instrument failure, and if so, the pathology or instrument failure type(s), and at least one of (i) pre-operative images, (ii) post-operative images, (iii) clinically relevant quantitative data, or (iv) surgical plan, including instrument geometry and placement. The data for each patient may further comprise the date or approximate time at which the patient developed a pathology or instrument failure. The data for each patient may further comprise images taken at different times following the surgery, for example, images taken at 6 months, 1, 2, 5, 10, or 15 years after the surgery.

In step 27, there is obtained from the database, a set of data having patients with similar pre-operative relationships of vertebral pairs, and a similar surgical plan to those of the subject. Artificial intelligence may be employed to determine a first risk of one or more pathology or instrument failure type for the subject based on correlations of the patients in this set to developed pathology or instrument failure types. Optionally, a risk may be provided for a time of onset for each pathology or instrument failure type.

In step 28, there is obtained from the database, a set of data having patients with similar post-operative relationships of vertebral pairs to the vertebral relationships in the predicted post-operative images of the subject. Artificial intelligence may be employed to determine a second risk of one or more pathology or instrument failure types for the subject based on correlations of the patients in this set to developed pathology or instrument failure types. Optionally, a risk may be provided for a time of onset for each pathology or instrument failure, generally with the date of the surgery being the defining reference point.

In step 29, it is obtained from the database, a set of data having patients with similar clinically relevant quantitative data and a similar surgical plan to those of the subject. Artificial intelligence may be employed to determine a third risk of one or more pathology or instrument failure types for the subject based on correlations of the patients in this set to developed pathology or instrument failure types. Optionally, a risk may be provided for a time of onset for each pathology or instrument failure type, generally with the date of the surgery being the defining reference point.

In step 30, artificial intelligence or machine learning is used to combine the first, second, third, and any additional previously determined risks of pathology or instrument failure types, to calculate an overall risk of one or more pathology or instrument failure types for the subject. A risk may be provided for each pathology, such as in the form of a percentage. Optionally, a risk may be provided for a time of onset for each pathology, such as, for instance, the probability that the subject will develop PJK ten years after the surgery.

In step 31, the system determines whether the one or more overall risks are excessive according to pre-defined rules of acceptability of overall risk level, for example, more than ten percent risk of any pathology.

If the risks are deemed excessive, this surgical plan is deemed unacceptable, and in step 32, an alternative spinal surgical plan is selected for pathology prediction analysis, and the system performs the selection routine again, and in step 33, the risk level result may optionally be output by the system.

Should the number of alternative spinal surgical plans exceed a predetermined level, the system may terminate the routine, since the sought-for surgical solutions selected may possibly be in an incorrect direction. It is appreciated by persons skilled in the art that the present disclosure is not limited by what has been particularly shown and described hereinabove. Rather the scope of the present disclosure includes both combinations and subcombinations of various features described hereinabove as well as variations and modifications thereto which would occur to a person of skill in the art upon reading the above description and which are not in the prior art.

I claim:

1. A method for determining an acceptable surgical plan for a subject using long term pathology prediction, comprising:
 (i) receiving, at a processor, (a) a spinal surgical plan that is to be performed on an operative region of a subject; (b) clinically relevant quantitative data of the subject; and (c) image data corresponding to pre-operative three-dimensional images of a spinal region of interest of the subject, the spinal region of interest comprising the operative region;
 (ii) determining, with the processor and based on the image data, an existing relationship between adjacent vertebrae of selected pairs of vertebrae within the spinal region of interest, the selected pairs of vertebrae being located both within and outside of the operative region;
 (iii) predicting, with the processor and based on the existing relationships and the spinal surgical plan, a post-operative relationship between the adjacent vertebrae of at least some of the selected pairs of vertebrae;
 (iv) accessing, with the processor, a database including a plurality of data sets, each data set associated with a patient of a plurality of patients and each data set comprising:
  post-operative pathology data on any pathology types developed by the patient; and
  input data comprising at least one of (a) pre-operative image data associated with the patient, (b) post-operative image data associated with the patient, (c) clinically relevant quantitative data associated with the patient, or (d) a surgical plan associated with the patient;
 (v) obtaining, with the processor and from the database, one or more data sets, from the plurality of data sets, that share a similarity with respect to at least one of the spinal surgical plan, the clinically relevant quantitative data of the subject, the existing relationship, or the predicted post-operative relationship;
 (vi) determining, with the processor and using the one or more data sets, one or more correlations between the post-operative pathology data and the input data;
 (vii) predicting, based on the one or more correlations and the similarity, a risk of the subject post-operatively developing any of the pathology types;
 (viii) inputting, by the processor, the predicted risks into an artificial intelligence engine to yield an overall risk of the subject developing one or more pathology types; and
 selecting an alternative spinal surgical plan returning to step (iii) if the overall risk for one or more pathology types for the subject has an unacceptable level.

2. The method of claim 1, further comprising outputting the overall risk for one or more pathology types for the subject.

3. The method of claim 1, wherein if the number of alternative spinal surgical plans selected exceeds a predetermined number, the method is terminated.

4. The method of claim 1, wherein at least one data set of the plurality of data sets further comprises data on any instrument failure types developed by the patient associated with the at least one data set, and the method further comprises calculating an overall risk of one or more instrument failure types for the spinal surgical plan for the subject.

5. The method of claim 4, wherein the instrument failure types comprise at least one of screw pull-out, excessive rod bending, or fractures or breakage of any of implants, screws, interbodies, or rods.

6. The method of claim 1, wherein one or more of the existing relationships or predicted post-operative relationships between selected pairs of vertebrae involves characteristics of a disc between a vertebral pair.

7. The method of claim 1, wherein the pre-operative three-dimensional images of the spinal region of interest of the subject comprise at least one of CT images, MRI images, X-ray images, or dynamic motion capture images.

8. The method of claim 1, wherein the clinically relevant quantitative data of the subject comprises at least one of (i) past medical history, (ii) age, (iii) BMI, (iv) gender, (v) comorbidity, (vi) ethnicity, or (vii) current clinical status, at least one of which is derived from qualitative data.

9. The method of claim 1, wherein at least some data sets of the plurality of data sets further comprise an approximate date of onset of pathology for the associated patients, and wherein step (vii) of claim 1 further comprises determining a conditional probability of the subject developing one or more pathology types at defined time points in the future.

10. The method of claim 9, wherein the defined time points in the future comprise at least one of (i) half a year after surgery, (ii) a year after the surgery, (iii) 2 years after the surgery, (iv) 5 years after the surgery, (v) 10 years after the surgery, or (vi) 15 years after the surgery.

11. The method of claim 1, wherein step (vii) of claim 1 is performed using at least one of artificial intelligence, predictive modeling, machine learning, deep learning, neural networks, or regression.

12. The method of claim 1, further comprising determining, with the processor and based on predefined rules, whether the overall risk is acceptable.

13. The method of claim 1, wherein the one or more data sets in step (v) comprise at least one data set for which a source of the similarity is the (a) pre-operative image data associated with the patient or the (d) surgical plan associated with the patient, and at least one data set for which the source of the similarity is the (b) post-operative image data associated with the patient.

14. The method of claim 1, wherein in step (v) of claim 1, a source of the similarity in at least one of the one or more data sets is at least one of the (a) pre-operative image data associated with the patient, (b) post-operative image data associated with the patient, (c) clinically relevant quantitative data associated with the patient, or (d) surgical plan associated with the patient.

15. The method of claim 1, wherein step (iii) of claim 1 further comprises predicting the post-operative relationship between the adjacent vertebrae of at least one of the selected pairs of vertebrae after a planned instrumentation.

16. The method of claim 1, wherein a probability of the overall risk is determined using machine learning or artificial intelligence.

17. The method of claim 1, wherein the spinal region of interest of the subject is more extensive than the operative region of the spinal surgical plan.

18. A method for determining an acceptable surgical plan for a subject using long term pathology prediction, comprising:
   (i) receiving, at a processor, (a) a spinal surgical plan that is to be performed on an operative region of a subject; (b) clinically relevant quantitative data of the subject; and (c) image data corresponding to pre-operative three-dimensional images of a spinal region of interest of the subject, the spinal region of interest comprising the operative region;
   (ii) determining, with the processor and based on the image data, an existing relationship between adjacent vertebrae of selected pairs of vertebrae within the spinal region of interest, the selected pairs of vertebrae being located both within and outside of the operative region;
   (iii) predicting, with the processor and based on the existing relationships and the spinal surgical plan, a post-operative relationship between the adjacent vertebrae of at least some of the selected pairs of vertebrae;
   (iv) accessing, with the processor, a database including a plurality of data sets, each data set associated with one of a plurality of patients and each data set comprising: post-operative pathology data on any pathology types developed by the patient; and
      input data comprising at least one of (a) pre-operative image data associated with the patient, (b) post-operative image data associated with the patient, (c) clinically relevant quantitative data associated with the patient, or (d) a surgical plan associated with the patient;
   (v) obtaining, with the processor and from the database, one or more data sets, from the plurality of data sets, that share a similarity with respect to at least one of the spinal surgical plan, the clinically relevant quantitative data of the subject, the existing relationship, or the predicted post-operative relationship;
   (vi) determining, with the processor and using the one or more data sets, one or more correlations between the post-operative pathology data and the input data;
   (vii) predicting, based on the one or more correlations and the similarity, a risk of the subject post-operatively developing any of the pathology types; and
   (viii) inputting, by the processor, the predicted risks into an artificial intelligence engine to yield an overall risk of the subject developing one or more pathology types, wherein at least one of the existing relationships or the predicted post-operative relationships between adjacent vertebrae of the selected pairs of vertebrae comprise one or more of (i) angle between endplates, (ii) distance between vertebrae, (iii) shape or volume of intervertebral space, and (iv) degree of rotation or translation of one vertebra of each selected pair of vertebrae relative to the long axis of the spine, coronal axis of the spine, or sagittal axis of the spine, relative to this measurement for the adjacent vertebra of the selected pair.

19. A method for determining an acceptable surgical plan for a subject using long term pathology prediction, comprising:
   (i) receiving, at a processor, (a) a spinal surgical plan that is to be performed on an operative region of a subject; (b) clinically relevant quantitative data of the subject; and (c) image data corresponding to pre-operative three-dimensional images of a spinal region of interest of the subject, the spinal region of interest comprising the operative region;
   (ii) determining, with the processor and based on the image data, an existing relationship between adjacent vertebrae of selected pairs of vertebrae within the spinal region of interest, the selected pairs of vertebrae being located both within and outside of the operative region;
   (iii) predicting, with the processor and based on the existing relationships and the spinal surgical plan, a post-operative relationship between the adjacent vertebrae of at least some of the selected pairs of vertebrae;
   (iv) accessing, with the processor, a database including a plurality of data sets, each data set associated with one of a plurality of patients and each data set comprising: post-operative pathology data on any pathology types developed by the patient; and
      input data comprising at least one of (a) pre-operative image data associated with the patient, (b) post-operative image data associated with the patient, (c) clinically relevant quantitative data associated with the patient, or (d) a surgical plan associated with the patient;
   (v) obtaining, with the processor and from the database, one or more data sets, from the plurality of data sets, that share a similarity with respect to at least one of the spinal surgical plan, the clinically relevant quantitative data of the subject, the existing relationship, or the predicted post-operative relationship;
   (vi) determining, with the processor and using the one or more data sets, one or more correlations between the post-operative pathology data and the input data;
   (vii) predicting, based on the one or more correlations and the similarity, a risk of the subject post-operatively developing any of the pathology types; and
   (viii) inputting, by the processor, the predicted risks into an artificial intelligence engine to yield an overall risk of the subject developing one or more pathology types, wherein the step of determining one or more correlations between the pathology data and the input data is performed using at least one of (i) Pearson correlation coefficient, (ii) Pearson's product-moment coefficient, (iii) linear regression analysis, or (iv) Spearman Rank Correlation.

* * * * *